United States Patent
Couturier et al.

(10) Patent No.: US 6,534,684 B1
(45) Date of Patent: Mar. 18, 2003

(54) TRIS[(1H,1H,2H,2H-PERFLUOROALKYL) ARYL]PHOSHITES AND CATALYTIC USES THEREOF

(75) Inventors: Jean-Luc Couturier, Lyons (FR); Thomas Mathivet, Lille (FR); Eric Monflier, La Madeleine (FR); Yves Castanet, Hem (FR); André Mortreux, Hem (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 09/913,166
(22) PCT Filed: Feb. 9, 2000
(86) PCT No.: PCT/FR00/00310
 § 371 (c)(1),
 (2), (4) Date: Dec. 7, 2001
(87) PCT Pub. No.: WO00/47590
 PCT Pub. Date: Aug. 17, 2000

(30) Foreign Application Priority Data

Feb. 10, 1999 (FR) .............................................. 99 01552

(51) Int. Cl.[7] .................................................. C07F 9/06
(52) U.S. Cl. ......................................................... 568/16
(58) Field of Search ............................................ 568/16

(56) References Cited

U.S. PATENT DOCUMENTS 4,528,167 A * 7/1985 Preston et al. ............... 423/139
5,463,082 A * 10/1995 Horvath et al. ................ 549/46

FOREIGN PATENT DOCUMENTS

WO   WO 98/32533   7/1998

OTHER PUBLICATIONS

D. Sinou et al., A Convenient Access to Triarylphosphines with Fluorous Phase Affinity, *Tetrahedron Letters*, vol. 40, No. 5, Jan. 29, 1999, pp. 849–852.

R. King et al., "Palladium (0) –Catalyzed Substitutuion of Allylic Substrates Substrates in Perfluorinated Solvents" *Tetrahedron Letters*, NL, Elsevier Science, vol. 39, No. 51, Dec. 17, 1998, pp. 9439–9442.

* cited by examiner

Primary Examiner—Ceila Chang
Assistant Examiner—Golam M M Shameem
(74) Attorney, Agent, or Firm—Young & Thompson

(57) ABSTRACT

A method for preparing tris[(1H,1H,2H,2H-perfluoroalkyl) aryl]phosphites consists in preparing a grignard reagent from an alkoxyhalogenobenzene, then reacting it with a iodo-1H,1H,2H,2H-perfluoroalkane; transforming the alkoxy function of (1H,1H,2H,2H-perfluoroalkyl) alkoxybenzene obtained into a hydroxy function, then reacting (1H,1H,2H,2H-perfluoroalkyl)hydroxybenzene with $PCl_3$. The invention also concerns fluorinated arylphosphites and their use as transition metal ligand for making catalysts to be used in two-phase catalysis with fluorinated phase.

2 Claims, No Drawings

TRIS[(1H,1H,2H,2H-PERFLUOROALKYL) ARYL]PHOSHITES AND CATALYTIC USES THEREOF

This application is a 371 of PCT/FR00/00310 Feb. 9, 2000.

TECHNICAL FIELD

The present invention relates to a process for preparing tris[(1H,1H,2H,2H-perfluroalkyl)aryl] phosphites, referred to hereinbelow as fluorine-containing aryl phosphites.

The present invention also relates to the said fluorine-containing aryl phosphites and to their uses in particular in two-phase catalysis with a fluorine-containing phase.

PRIOR ART

This two-phase catalysis with a fluorine-containing phase has been described by Istvan T. Horwath et al. in patent U.S. Pat. No. 5,463,082.

The general concept of this catalysis is based on the use of a fluorinated phase which is immiscible with an organic phase without heating and generally miscible when heated.

The fluorinated phase is a solvent rich in C-F bonds (fluorocarbons or hydrofluorocarbons).

When not heated, the system consists of two phases:

a fluorinated phase which is a solvent rich in C-F bonds and which contains a catalyst made soluble in said fluorine-containing solvent by means of fluorine-containing chains, a hydrocarbon-based organic phase, which is immiscible with the fluorine-containing phase, and which contains the reagents.

The catalysis reaction is carried out with heating in a phase which is generally homogeneous, that is to say that above a certain temperature a single phase is generally obtained in which the catalysis takes place. Once the reaction is complete, the catalysis is readily recovered by cooling the reaction medium to a temperature below the temperature of miscibility of the two phases.

Thus, in order to make the catalyst preferentially soluble in the fluorine-containing phase, it has been recommended to functionalize it with one or more perfluoroalkyl groups.

The perfluoroalkyl groups of the fluorine-containing phosphites used as coordination ligands have electron-withdrawing properties which may influence the coordination characteristics of the phosphorus atom and thus adversely modify the catalytic activity of the catalysts made with such fluorine-containing ligands.

In order to reduce these adverse effects of the perfluoroalkyl chains on the phosphorus atom, it has been proposed to introduce non-fluorine-containing groups known as "spacers" between the phosphorus atom and said perfluoroalkyl chain.

Examples of such spacers which may be mentioned are polymethylene radicals $(CH_2)_n$ with n ranging from 1 to 3 and the phenylene radical $-C_6H_4-$.

As illustrations of fluorine-containing phosphites containing such spacers, mention will be made of tris (1H,1H,1H,2H,2H-perfluoroalkyl) phosphite mentioned by I. T. Horwath et al. in patent U.S. Pat. No. 5,463,082; tris(4-tridecafluorohexylphenyl) phosphite mentioned by E. G. Hope et al. in J. Chem. Soc. Perkin Trans. 1. 1997, pages 3609–3612, and the tris(perfluoroalkylphenyl) phosphites mentioned by T. Mathivet et al. in Tetrahedron Letters 39, 1998, pages 9411–9414.

In general, these fluorine-containing phosphites are obtained with low yields, by processes using expensive reagents and with long reaction times (several days) in particular, for the aryl phosphites containing perfluoroalkyl chains.

Thus, for example, E. G. Hope et al. (J. Chem. Soc. Perkin Trans. 1, 1997, pages 3609–3612) obtain tris(4-tridecafluorohexylphenyl) phosphite by synthesizing, in a first step, 4-tridecafluorophenol by reacting $C_6F_{13}I$ dissolved in hexafluorobenzene with para-iodophenol in the presence of copper in DMSO at 80° C., under nitrogen for 6 days. In a second step, the 4-tridecafluorophenol, obtained in a yield of 63%, is introduced slowly with triethylamine into a solution of $PCl_3$ in $Et_2O$. The tris(4-tridecafluorohexylphenyl) phosphite is obtained in a yield of 55.7%, ie an overall yield of 35%.

Mathivet et al. (Tetrahedron Letters, 39, 1998, pages 9411–9414) also use the reaction of a perfluoroalkyl iodide with bromophenol or iodophenol to obtain the (perfluoroalkyl)phenols, but they perform the process in DMSO. They obtain the (perfluoroalkyl)phenols in yields ranging from 23% for 2-methyl-4-perfluorooctylphenol to 70% for 4-perfluorooctylphenol.

The use of the reaction between an iodophenol or bromophenol and an iodoqerfluoroalkyl in the presence of copper (Ullmann reaction) does not allow 1H,1H,2H,2H-perfluoroalkyl groups to be introduced onto the phenol nucleus.

Japanese patent application JP 7-179 384 describes the production of 4-(1H,1H,2H,2H-perfluoroalkyl)phenol by carrying but the following reactions:

reaction of an alcohol $CF_3(CH_2)_pCH_2CH_2OH$ with triflic acid to give an ester of formula: $CF_3(CH_2)_p CH_2CH_2OSO_2CF_3$ (with p=1 to 15), followed by reaction of said ester with a Grignard reagent obtained from magnesium and a p-alkoxyhalobenzene to give the 4-(1H,1H,2H,2H-perfluoroalkyl)-alkoxybenzene and, after cleavage of the alkoxy function, to give the 4-(1H,1H,2H,2H-perfluoroalkyl)-phenol in yields in the region of 50%.

However, performing the process in this way has the drawback of using expensive reagents: the alcohols $CF_3(CF_2)_pCH_2CH_2OH$ and triflic acid, the latter also being difficult to handle.

DESCRIPTION OF THE INVENTION

A process has now been found for preparing tris[(1H,1H,2H,2H-perfluoroalkyl)phenyl] phosphites of formula (I):

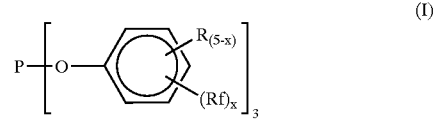

(I)

in which the (5-x)R, which may be identical or different, represent a hydrogen atom, a linear or branched alkyl radical containing a number of carbon atoms ranging from 1 to 10; a halogen atom such as bromine or chlorine; Rf represents a 1H,1H,2H,2H-perfluoroalkyl radical $C_nF_{2n+1}C_2H_4-$ with n ranging from 4 to 20 and preferably ranging from 8 to 20, x is an integer ranging from 1 to 5 and preferably ranging from 1 to 3; characterized in that it comprises the steps consisting in:

a) preparing a Grignard reagent of formula (II)

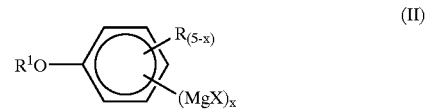

(II)

from an alkoxyhalobenzene of formula (III):

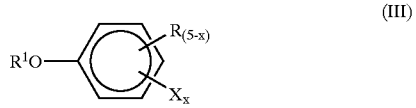

in which formulae $R^1$ represents a linear or branched alkyl radical containing a number of carbon atoms ranging from 1 to 6 and preferably ranging from 1 to 3, X represents a bromine, chlorine or iodine atom, R and x having the same meanings as in formula (I), followed by reacting said compound (II) with a 1-iodo-1H,1H,2H,2H-perfluoroalkane $C_nF_{2n+1}C_2H_4I$ (IV), represented hereinbelow by RfI, to give a (1H,1H,2H,2H-perfluoroalkyl)alkoxybenzene (V):

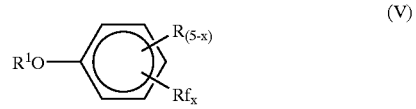

c) converting the alkoxy function $R^1O—$ of (V) obtained in step a) into a hydroxyl function $HO^-$ to give a (1H,1H,2H,2H-perfluoroalkyl)hydroxybenzene of formula (VI):

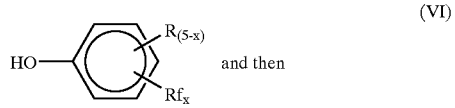

and then d) reacting compound (VI) obtained in step b) with $PCl_3$ to give the tris[(1H,1H,2H,2H-perfluoroalkyl)phenyl] phosphite (I).

The Grignard reagent (II) is obtained according to methods known to those skilled in the art, which consist in reacting an alkoxyhalobenzene of formula (III) with magnesium in an ethereal solvent such as diethyl ether or THF at room temperature.

Preferably, X represents a bromine atom.

As illustrations of bromoalkoxybenzenes which may be used according to the present invention, mention will be made of 4-bromoanisole, 3-bromoanisole, 2,4-dibromoanisole, 2,4,6-tribromoanisole, 4-bromo-2,6-dimethylanisole and 4-bromophenetole.

The reaction between the Grignard reagent (II) and the iodofluoro compound RfI is carried out in the presence of copper iodide CuI used in weight amounts ranging from 0.1% to 10% relative to the compound RfI.

Preferably, the ethereal solution of the Grignard reagent is introduced slowly into an ethereal suspension of RfI plus CuI at a temperature in the region of 0° C. and, once the addition is complete, the reaction medium is then maintained at 20–30° C. with stirring for a period of not more than 6 hours and preferably between 1 and 3 hours.

Then, the medium is hydrolyzed and the compound (V) is isolated according to methods known to those skilled in the art (extraction, washing, drying and removal of the solvent under reduced pressure).

As illustrations of RfI which may be used according to the present invention, mention will be made of 1-iodo-1H,1H,2H,2H-perfluorodecane $CF_3(CH_2)_7CH_2CH_2I$ and 1-iodo-1H,1H,2H,2H-perfluorooctane $CF_3(CH_2)_5CH_2CH_2I$.

The cleavage of the alkoxy function $R^1O$ in compound (V), step b) is carried out by methods known to those skilled in the art, in particular using boron tribromide $BBr_3$ in an organic solvent such as benzene or toluene at a temperature of between 60° C. and 100° C. and preferably between 70° C. and 90° C.

The reaction medium obtained is then cooled, after which it is introduced into water. The hydroxylated compound (VI) is isolated in a known manner.

According to the process of the present invention, $BBr_3$ is used in a molar ratio: compound (V)/$BBr_3$ of between 1 and 1.5 and preferably between 1.2 and 1.4.

The reaction between compound (VI) and $PCl_3$, step c), is carried out in an organic solvent such as THF or diethyl ether $Et_2O$, in the presence of a tertiary base such as pyridine or triethylamine.

The process is performed at low temperature, −10° C. to 0° C., by introducing $PCl_3$ into a medium containing an organic solvent, the tertiary base and the fluorophenol compound (VI).

Once the addition is complete, the reaction medium is allowed to return to a temperature of about +20° C. to +30° C. and the medium is then maintained at this temperature with vigorous stirring for several hours. Next, the mixture is filtered and the fluorine-containing aryl phosphite (I) is isolated from the filtrate by removing the organic solvent under reduced pressure.

The compounds obtained in steps a), b) and c) may be identified by elemental analysis, proton, $^{19}F$, $^{13}C$ and $^{31}P$ NMR and by mass spectrometry (MS).

The process according to the present invention has the advantage of obtaining fluorine-containing aryl phosphites (I) in good yields from commercially available reagents.

Another subject of the invention concerns tris[(1H,1H,2H,2H-perfluoroalkyl)phenyl] phosphites of formula (I) described above.

Among the compounds of formula (I) that are preferred are those in which x=1, 2 or 3, R=H or $CH_3—$ and Rf=$CH_3(CF_2)_7C_2H_4—$.

As representatives of such compounds, mention will be made most particularly of tris[4-(1H,1H,2H,2H-perfluorodecyl)phenyl] phosphate, tris[2-(1H,1H,2H,2H-perfluorodecyl)phenyl] phosphite, tris[2,4-bis(1H,1H,2H,2H-perfluorodecyl)phenyl] phosphite, or tris[3-(1H,1H,2H,2H-perfluoroalkyl)-5-chlorophenyl] phosphite, which are particularly preferred and whose manufacturing process and spectroscopic characteristics are detailed in Examples 1 to 4 below.

The fluorine-containing aryl phosphites (I) are resistant to hydrolysis and highly soluble in perfluorinated solvents, which allows them to be used advantageously as transition metal ligands for preparing catalysts which may be used in particular in two-phase catalysis with a fluorine-containing phase to carry out chemical reactions of hydroformylation, of hydrogenation of unsaturated compounds, of carbonylation, telomerization and cyclodimerization of dienes, and of hydrocyanation of olefins or conjugated dienes.

Another subject of the invention is thus the use of the tris[(1H,1H,2H,2H-perfluoroalkyl)phenyl] phosphites of formula (I) as transition metal ligands for the preparation of catalysts for the abovementioned chemical reactions.

As examples of transition metals which may be used according to the present invention, mention will be made of rhodium, palladium, ruthenium, nickel, iridium, chromium, cobalt and iron.

The catalysts obtained with the fluorine-containing phosphites (I) of the present invention used as ligands have the advantage of being readily separated out and recycled when they are used in fluorine-containing two-phase catalysis.

In addition, the Applicant has found that, during the hydroformylation reaction of olefins, and in particular during the hydroformylation of 1-decene with a catalyst of the rhodium type complexed with tris[4-(1H,1H,2H,2H-perfluorodecyl)phenyl) phosphite, said catalyst can be recycled without any loss of catalytic activity.

The catalyst according to the present invention may be prepared in situ, that is to say in the reactor in which the chemical reaction is carried out, by mixing the transition metal, generally in the form of a metal complex or a metal salt, with the compounds of formula (I) obtained according to the process of the present invention, or alternatively may be prepared and isolated separately.

The examples which follow illustrate the invention.

EXAMPLES

The following reagents are used:
magnesium powder (sold by the company Aldrich)
anhydrous THF distilled over sodium/benzophenone under an atmosphere of inert gas (nitrogen)
bromoanisole (Aldrich) for the synthesis of Example 1
2-bromoanisole (Aldrich) for the synthesis of Example 2
3,5-dichloroanisole (Aldrich) for the synthesis of Example 3
2,4-dibromoanisole (Aldrich) for the synthesis of Example 4
1-iodo-1H,1H,2H,2H-perfluorodecane, sold by the company Elf Atochem S.A. under the name Foralkyl EI-8 (Examples 1 to 4)
CuI (Aldrich)
silica gel, 70–230 mesh, 60 Å (Aldrich)
BBr$_3$ (Aldrich)
PCl$_3$ (Aldrich)
triethylamine (sold by the company Acros), distilled over CaH$_2$ under nitrogen
Rh(acac)(CO$_2$) for Rh(acetylacetonate)(CO)$_2$ (Aldrich)
1-decene (Acros)
n-undecane (Acros)

The compounds obtained were characterized by elemental analysis and by $^1$H, $^{13}$C, $^{31}$P and $^{19}$F NMR.

The NMR spectra were acquired on a Brucker AC 100 machine ($^1$H, 100 MHz; $^{31}$P, 40.53 MHz; $^{19}$F, 94.22 MHz; $^{13}$C, 25.18 MHz). The $^{13}$C and $^{31}$P NMR spectra are acquired with $^1$H decoupling.

The chemical shifts δ are given in ppm relative to tetramethylsilane (internal reference) for the proton and carbon, relative to 85% H$_3$PO$_4$ (external reference) for phosphorus and relative to trifluoroacetic acid for fluorine.

In Tables 1 et seq.:
S ald denotes the selectivity towards aldehydes
Isom denotes the selectivity towards 1-decene isomers
n means the number of moles of linear aldehyde
i means the number of moles of branched aldehyde

Example 1

Preparation of tris[4-(1H,1H,2H,2H-Perfluorodecyl)-phenyl] Phosphite

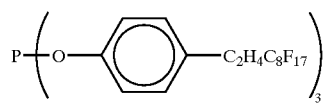

a) Preparation of 4-(1H,1H,2H,2H-perfluorodecyl)-anisole

439 mg (18.06 mmol) of magnesium powder are dried under vacuum for 1 hour in a 250 ml round-bottom flask fitted with a reflux condenser and a side tube. The assembly is placed under nitrogen. 25 ml of anhydrous THF are added. About half of the 3.375 g (18.06 mmol) of 4-bromoanisole is added under nitrogen to the suspension of Mg in THF and the remainder of the 4-bromoanisole is diluted with 5 ml of THF. 2 or 3 drops of bromoethane are added to the flask containing the magnesium, and the reaction starts instantaneously. The rest of the 4-bromoanisole solution is added dropwise over 15 minutes to the Mg suspension. The reaction is left for about 1 hour.

10.356 g (18.06 mmol) of iodo-1H,1H,2H,2H-perfluorodecane and 340 mg (1.8 mmol) of copper iodide CuI are then dissolved in 20 ml of anhydrous THF. The magnesium solution is poured dropwise at 0° C. over 1 hour to the suspension of C$_8$F$_{17}$C$_2$H$_4$I and CuI. The mixture is allowed to return to room temperature and is stirred for 3 hours.

The resulting mixture is hydrolyzed with a solution of 10 ml of 37% hydrochloric acid in 50 ml of water. This mixture is stirred for 15 minutes. 50 ml of ether are added and the organic phase is recovered. The aqueous phase is extracted with 3×30 ml of ether. The organic phases are combined and washed with aqueous sodium thiosulfate solution (10 g of Na$_2$S$_2$O$_3$ in 100 ml of water). The organic phase is then dried over sodium sulfate for 30 minutes, filtered and evaporated under reduced pressure.

The product is purified by chromatography on a column (h=55 cm/Ø=5 cm) of silica gel (70–230 mesh, 60 Å) with a mixture of petroleum ether/dichloromethane (80/20) as eluent (R$_F$=0.67).

After evaporation of the fractions that are identical on TLC, 6.256 g of a white solid with a melting point of 35° C. are obtained. The yield of 4-(1H,1H,2H,2H-perfluorodecyl) anisole is 65% relative to the 4-bromoanisole used.

$^1$H NMR (CDCl$_3$) δ (ppm): 7.13 (2H, m, J=8.6 Hz, J'=2.5 Hz, 3.5-ArH), 6.86 (2H, m, J=8.6 Hz, J'=2.5 Hz, 2.6-ArH), 3.79 (2H, s, —OCH$_3$), 2.86 (2H, m, $^3$J$_{HH}$=8.4 Hz, —CH$_2$—CH$_2$—C$_8$F$_{17}$), 2.33 (2H, tt, $^3$J$_{HF}$=18.3 Hz, $^3$J$_{HH}$=8.4 Hz, —CH$_2$—CH$_2$—C$_8$F$_{17}$).

$^{19}$F NMR (CDCl$_3$) δ (ppm): −81.13 (3F, t, J=9.5 Hz, —CF$_3$), −114.99 (2F, t, J=12.9 Hz, —CF$_2$—), −122.02 (2F, m, —CH$_2$—), −122.24 (4F, m, 2x—CH$_2$—), −123.04 (2F, m, —CF$_2$—), −123.82 (2F, m, —CF$_2$—), −126.45 (2F, m, —CF$_2$—).

$^{13}$C NMR (CDCl$_3$) δ (ppm): 154.32 (s, 1-C arom), 131.51 (s, 4-C arom), 129.57 (s, 3,5-CH arom), 114.30 (s, 2,6-CH arom), 55.21 (s, —OCH$_3$), 33.41 (t, $^2$J$_{CF}$=22.0 Hz, —CH$_2$—CH$_2$—C$_8$F$_{17}$), 25.69 (s, —CH$_2$—CH$_2$—C$_8$F$_{17}$)+complex signals —CF$_2$— and —CF$_3$.

SM m/e: 554: M$^+$ (17.3%), 535: M$^+$ —F (6.3 %) 134: M$^+$ —H—C$_8$F$_{17}$ (3.7%), 121: M$^+$ —CH$_2$C$_8$F$_{17}$ (100%), 69: CF$_3^+$ (2.0%).

Elemental analysis calculated for C$_{17}$H$_{11}$F$_{17}$O: C: 36.85%; H: 1.98% found: C: 38.11%; H: 2.14%.

b) Preparation of 4-(1H,1H,2H,2H-perfluorodecyl)-phenol

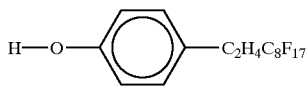

5.00 g (9.02 mmol) of 4-(1H,1H,2H,2H-perfluorodecyl)-anisole are dissolved, under nitrogen, in 40 ml of anhydrous toluene. 1.1 ml (11.73 mmol) of boron tribromide are taken up by syringe and diluted in 10 ml of anhydrous toluene. The $BBr_3$ solution is run in dropwise and at room temperature over 15 minutes to the fluoroanisole solution. The mixture is stirred vigorously for 2 hours at room temperature and then for 2 hours at 80° C.

The reaction mixture is cooled to room temperature and poured into 50 ml of water. 50 ml of ether are added and the organic phase is recovered. The aqueous phase is extracted with 3 times 30 ml of ether. The organic phase is then dried over sodium sulfate for 30 minutes, filtered and evaporated under vacuum.

The product is purified by chromatography on a column (h=55 cm; Ø=5 cm) of silica gel (70–230 mesh, 60 Å) with pure dichloromethane as eluent ($R_F$=0.48).

After evaporation of the fractions that are identical on TLC, 3.799 g of a white solid with a melting point of 88° C. are obtained. The yield of 4-(1H,1H,2H,2H-perfluorodecyl) anisole relative to the methoxy compound used is 78%.

$^1$H NMR ($CDCl_3$) δ (ppm): 7.08 (2H, m, J=8.5 Hz, J'=2.5 Hz, 3.5-ArH), 6.78 (2H, m, J=8.5 Hz, J'=2.5 Hz, 2.6-ArH), 4.75 (1H, s, —OH), 2.84 (2H, m, $^3J_{HH}$=8.4 Hz, —$CH_2$—$CH_2$—$C_8F_{17}$), 2.32 (2H, tt, $^3J_{HH}$=18.3 Hz, $^3J_{HH}$=8.4 Hz, —$CH_2$—$CH_2$—$C_8F_{17}$).

$^{19}$F NMR ($CDCl_3$) δ (ppm): −81.08 (3F, t, J=9.7 Hz, —$CF_3$), −114.93 (2F, t, J=12.5 Hz, —$CF_2$—), −121.99 (2F, m, —$CF_2$—), −122.21 (4F, m, 2×—$CF_2$—), −123.00 (2F, m, —$CF_2$—), −123.78 (2F, m, —$CF_2$—), −126.41 (2F, m, —$CF_2$—).

$^{13}$C NMR ($CDCl_3$) δ (ppm): 154.32 (s, 1-C arom), 131.51 (s, 4-C arom), 129.57 (s, 3,5-CH arom), 115.69 (s, 2,6-CH arom), 33.31 (t, $^2J_{CF}$=21.8 Hz, —$CH_2$—$CH_2$—$C_8F_{17}$), 25.67 (s, —$CH_2$—$CH_2$—$C_8F_{17}$)+complex signals —$CF_2$— and —$CF_3$.

SM m/e: 540: $M^+$ (4.7%), 521: $M^+$ —F (2.5%); 120: $M^+$ —H—$C_8F_{17}$ (3.1%), 107: $M^+$ —$CH_2C_8F_{17}$ (100%), 69: $CF_3^+$ (0.5%).

Elemental analysis calculated for $C_{16}H_9F_{17}O$: C: 35.58%; H: 1.66% found: C: 36.63%; H: 1.80%.

c) Production of tris[4-(1H,1H,2H,2H-Perfluorodecyl) phenyl] Phosphite

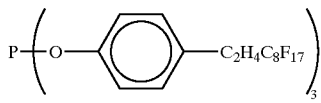

3 g of 4-(1H,1H,2H,2H-perfluorodecyl)phenol are dried by azeotropic distillation with 50 ml of toluene (distilled over sodium/benzophenone under nitrogen) at atmospheric pressure and under nitrogen. The solid is placed under vacuum (about 4 hours) while heating occasionally with a hair dryer to remove the residual traces of toluene, to constant mass.

0.2 ml of phosphorus trichloride $PCl_3$ (332.6 mg; 2.42 mmol) is weighed out under nitrogen and diluted with 15 ml of THF.

The solution is cooled to 0° C. using an ice bath and the $PCl_3$ solution is run in dropwise over 1 hour 30 minutes under nitrogen onto the phenolic solution. The resulting mixture is stirred vigorously at room temperature for 4 hours.

An assembly for filtration of ligands on silica is prepared. The silica stored in an oven at 100° C. is drawn down under vacuum while heating the assembly with a hair dryer. The assembly is placed under nitrogen and the crude reaction mixture is transferred onto the silica and eluted with 40 ml of THF. The filtrate obtained is evaporated under vacuum, to constant mass.

2.969 g of tris[4-(1H,1H,2H,2H-perfluorodecyl)phenyl] phosphite are obtained in the form of a white solid melting at 83° C. The yield is 97%.

$^{31}$P NMR ($CDCl_3$) δ (ppm): +127.95.

$^1$H NMR ($CDCl_3$) δ (ppm): 7.16 (2H, m, J=8.7 Hz, J'=2.5 Hz, 3.5 ArH), 7.10 (2H, m, J=8.7 Hz, J'=2.5 Hz, 2.6 ArH), 2.89 (2H, m, $^3J_{HH}$=8.4 Hz, —$CH_2$—$CH_2$—$C_8F_{17}$), 2.34 (2H, tt, $^3J_{HF}$=18.1 Hz, $^3J_{HH}$=8.4 Hz, —$CH_2$—$CH_2$—$C_8F_{17}$).

$^{19}$F NMR ($CDCl_3$) δ (ppm): −81.61 (9F, t, J=9.7 Hz, 3×—$CF_3$), −115.19 (6F, t, J=12.8 Hz, 3×—$CF_2$—), −122.24 (6F, m, 3×—$CF_2$—), −122.49 (12F, m, 6×—$CF_2$—), −123.32 (6F, m, 3×—$CF_2$—), −124.02 (6F, m, 3×—$CF_2$—), −126.82 (6F, m, 3×—$CF_2$—).

$^{13}$C NMR ($CDCl_3$) δ (ppm): 150.46 (d, $^2J_{CP}$=2.9 Hz, 1-C arom), 133.35 (s, 4-C arom), 129.69 (s, 3.5-CH arom), 121.16 (d, $^3J_{CP}$=6.7 Hz, 2.6-CH arom), 33.16 (t, $^2J_{CF}$=22.0 Hz, —$CH_2$—$CH_2$—$C_8F_{17}$), 25.92 (s, —$CH_2$—$CH_2$—$C_8F_{17}$)+complex signals —$CF_2$— and —$CF_3$.

Elemental analysis % calculated for $C_{48}H_{24}F_{51}O_3P$: C: 34.98%; H: 1.45% found: C: 35.67%; H: 1.60%.

Examples 2 to 4

Preparation of tris[2-(1H,1H,2H,2H-Perfluorodecyl)-phenyl] Phosphite, tris[3-Chloro-5-(1H,1H,2H,2H-perfluorodecyl)phenyl] Phosphite and tris[2,4-bis-(1H,1H,2H,2H-Perfluorodecyl) phenyl] Phosphite The three phosphites mentioned above were synthesized according to a procedure similar to that described in Example 1.

Characteristics of the Phosphites tris[2-(1H,1H,2H,2H-perfluorodecyl)phenyl] phosphite (Example 2)

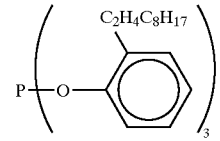

White Solid Melting at 68° C.

$^{31}$P{$^1$H} NMR ($CDCl_3$) δ (ppm): +132.71 (s).

$^1$H NMR ($CDCl_3$) δ (ppm): 7.22 (3H, br d, J=8.0 Hz, 3×3-ArH), 7.18 (6H, um, 3×4 and 5-ArH), 7.09 (3H, m, J=8.0 Hz, 3×6-ArH), 2.85 (6H, m, $^3J_{HH}$=8.2 Hz, 3×—$CH_2$—$CH_2$—$C_8F_{17}$), 2.26 (6H, tt, $^3J_{HF}$=18.4 Hz, $^3J_{HH}$=8.2 Hz, 3×—$CH_2$—$CH$—$C_8F_{17}$).

$^{19}$F{$^1$H} NMR ($CDCl_3$) δ (ppm): −81.39 (9F, t, $^3J_{FF}$=9.8 Hz, 3×—$CF_3$), −115.49 (6F, um, 3×—$CF_2$— α to the —$CH_2$—), −122.28 (6F, um, —$CF_2$—), −122.49 (12F, um, 6×—$CF_2$—), −123.29 (6F, um, 3×—$CF_2$—), −123.97 (6F, um, 3×—$CF_2$—), −126.71 (6F, um, 3×—$CF_2$—).

$^{13}$C{$^1$H} NMR ($CDCl_3$) δ (ppm): 149.93 (d, $^2J_{CP}$=3.0 Hz, 1-C arom), 130.79 (s, 3-CH arom), 130.60 (d, $^3J_{CP}$=1.9 Hz, 2-C arom), 128.27 (s, 5-CH arom), 124.79 (s, 4-CH arom), 119.86 (d, $^3J_{CP}$=13.3 Hz, 6-CH arom), 31.15 (t, $^2J_{CF}$=22.0 Hz, —$CH_2$—$CH_2$—$C_8F_{17}$), 21.57 (t, $3J_{CF}$=3.8 Hz, —$CH_2$—$CH_2$—$C_8F_{17}$)+complex signals —$CF_2$— and —$CF_3$ (105–120).

tris[3-(1H,1H,2H,2H-Perfluorodecyl)-5-chlorophenyl] Phosphite (Example 3)

White Solid Melting at 58° C.

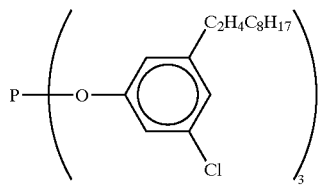

$^{31}P\{^1H\}$ NMR (CDCl$_3$) δ (ppm): +126.53 (s).

$^1$H NMR (CDCl$_3$) δ (ppm): 7.02 (6H, um, 3×2 and 4-ArH), 6.82 (3H, um, 3×6-ArH), 2.86 (6H, m, $^3J_{HH}$=8.3 Hz, 3×—CH$_2$—CH$_2$—C$_8$F$_{17}$), 2.32 (6H, m, $^3J_{HF}$=18.1 Hz, $^3J_{HH}$=8.3 Hz, 3×—CH$_2$—CH$_2$—C$_8$F$_{17}$).

$^{19}$F$\{^1$H$\}$ NMR (CDCl$_3$) δ (ppm): -81.10 (9F, t, $^3J_{FF}$=9.8 Hz, 3×—CF$_3$), -114.91 (6F, um, 3×—CF$_2$— α to the —CH$_2$—), -122.04 (6F, um, 3×—CF$_2$—), -122.26 (12F, um, 6×—CF$_2$—), 123.07 (6F, um, 3×—CF$_2$—), -123.74 (6F, um, 3×—CF$_2$—), -126.48 (6F, um, 3×—CF$_2$—).

$^{13}$C$\{^1$H$\}$ NMR (CDCl$_3$) δ (ppm): 152.00 (d, $^2J_{CP}$=2.4 Hz, 1-C arom), 142.63 (s, 5-C arom), 135.51 (s, 3-C arom), 124.97 (s, 4-CH arom), 119.55 (d, $^3J_{CP}$=7.3 Hz, 2-CH arom), 119.03 (d, $^3J_{CP}$=6.4 Hz, 6-CH arom), 32.49 (t, $^2J_{CF}$=22.1 Hz, —CH$_2$—CH$_2$—C$_8$F$_{17}$), 26.27 (t, $^3J_{CF}$=3.3 Hz, —CH$_2$—CH$_2$—C$_8$F$_{17}$)+complex signals —CF$_2$— and —CF$_3$ (105–120).

tris[2,4-bis[H,1H,2H,2H-Perfluorodecyl)phenyl] Phosphite (Example 4)

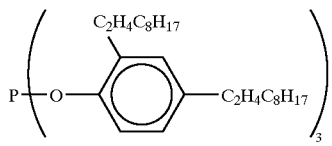

White Solid Melting at 54° C.

$^{31}$P$\{^1$H$\}$ NMR (CF$_2$ClCCl$_2$F, external lock on CDCl$_3$) δ (ppm): +129.87 (s).

$^1$H NMR (CF$_2$ClCCl$_2$F, external lock on CDCl$_3$) δ (ppm): 7.22 (3H, d, J=8.3 Hz, 3×6-ArH), 7.09 (3H, d, J'=1.8 Hz, 3×3-ArH), 7.06 (3H, dd, J=8.3 Hz, J'=1.8 Hz, 3×5-ArH), 2.87 (12H, um, 6×—CH$_2$—CH$_2$—C$_8$F$_{17}$), 2.32 (12H, um, 6×—CH$_2$—CH$_2$—C$_8$F$_{17}$).

$^{19}$F$\{^1$H$\}$ NMR (diethyl ether, external lock on CDCl$_3$) δ (ppm): -81.06 (18F, t, $^3J_{FF}$=9.3 Hz, 6×—CF$_3$), -114.92 (6F, um, 3×—CF$_2$— γ to 4-C arom), -115.15 (6F, um, 3×—CF$_2$— γ to 2-C arom), -122.22 (36F, um, 18×—CF$_2$—), -123.04 (6F, um, 3×—CF$_2$—), 123.22 (6F, um, 3×—CF$_2$—), -123.91 (12F, um, 6×—CF$_2$—), -126.40 (6F, um, 3×—CF$_2$—), -126.64 (6F, um, 3×—CF$_2$—).

$^{13}$C$\{^1$H$\}$ NMR (CF$_2$ClCCl$_2$F, external lock on CDCl$_3$) δ (ppm): 149.35 (s, 1-C arom), 136.68 (s, 4-C arom), 131.70 (br s, 2-C arom), 131.26 (s, 3-CH arom), 128.55 (s, 5-CH arom), 120.92 (d, $^3J_{CP}$=12.5 Hz, 6-CH arom), 33.71 (t, $^2J_{CF}$=22.1 Hz, —CH$_2$—CH$_2$—C$_8$F$_{17}$ β to 4-CH arom), 31.93 (t, $^2J_{CF}$=22.1 Hz, —CH$_2$CH$_2$—C$_8$F$_{17}$ β to 2-CH arom), 26.41 (br s, —CH$_2$—CH$_2$—C$_8$F$_{17}$ α to 4-C arom), 22.32 (br s, —CH$_2$—CH$_2$—C$_8$F$_{17}$ α to 2-C arom)+signal complexes —CF$_2$— and —CF$_3$ (105–120).

Example 5

Hydroformylation of 1-decene in Fluorine-containing Two-phase Medium

Reaction

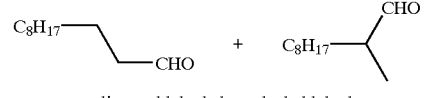

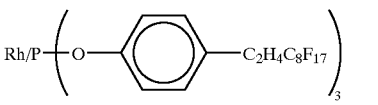

+isomers: 2-decene/3-decene/4-decene/5-decene solvent: C$_8$F$_{17}$H 10.0 mg (38.7 μmol) of Rh(acac)(CO)$_2$ and 319.0 mg (0.193 mmol) of tris[4-(1H,1H,2H,2H-perfluorodecyl)-phenyl] phosphite are dissolved under nitrogen in 15 ml of C$_8$F$_{17}$H (degassed 3 times consecutively by freezing). The mixture is stirred vigorously for about 2 hours (until the rhodium has completely dissolved).

10.856 g (77.4 mmol) of 1-decene and 1.2671 g (8.1 mmol) of n-undecane (internal standard for the gas chromatography analyses) are weighed out. Degassing is carried out 3 times consecutively by freezing. This solution and the catalytic solution are combined.

This mixture is introduced under nitrogen into a 50 ml autoclave placed beforehand under nitrogen. The heating is adjusted to 80° C., the stirring is adjusted to 1500 rpm and the pressure is adjusted to 40 bar of CO/H$_2$ (1:1). The pressure is kept constant throughout the reaction by means of a ballast.

Samples are taken regularly to monitor the reaction progress, and the results are collated in Table 1 below. The initial activity of the system is 2100 h$^{-1}$.

TABLE 1

| TIME (h) | CONVERSION (%) | n/i | S ald (%) | Isom (%) |
|---|---|---|---|---|
| 0.5 | 66 | 4.4 | 96 | 4 |
| 1 | 92 | 4.2 | 95 | 5 |
| 2 | 100 | 3.8 | 95 | 5 |

Examples 6 to 8

Hydroformylation of 1-decene in Fluorine-containing Two-phase Medium in the Presence of tris[2-(1H,1H,2H,2H-Perfluorodecyl)phenyl] Phosphite (Example 6), tris[3-Chloro-5-(1H,1H,2H, 2H-perfluorodecyl)phenyl] Phosphite (Example 7) and tris[2,4-bis(1H,1H,2H,2H-Perfluorodecyl) phenyl] Phosphite (Example 8)

The hydroformylation of 1-decene was carried out using three phosphites mentioned above, using the same procedure as in Example 5; the results are collated in Table 2.

TABLE 2

| Example No. | Fluorine-containing phosphite | Time (h) | Conversion | n/i | S ald (%) | Isom (%) |
|---|---|---|---|---|---|---|
| 6 | P-(-O-C6H3(C2H4C8F17))3 | 0.16 | 100 | 2.0 | 85 | 15 |
| 7 | P-(-O-C6H3(C2H4C8F17)(Cl))3 | 1 | 100 | 4.5 | 88 | 12 |
| 8 | P-(-O-C6H3(C2H4C8F17)(C2H4C8F17))3 | 0.15 | 100 | 2.0 | 85 | 15 |

Example 9

Recycling the Fluorine-containing Catalytic Chases in the Presence of tris[4-(1H,1H,2H,2H-Perfluorodecyl)-phenyl] Phosphite At the end of the catalytic test of Example 5, the autoclave is cooled in a bath of cold water, depressurized and a nitrogen atmosphere is then reestablished. The catalytic solution is transferred under nitrogen into a Schlenk tube and the organic phase is separated out by settling of the phases 30 minutes later. Similar amounts of decene and of undecane are again weighed out and then added to the recycled fluorine-containing phase. The recycling test is then carried out in the same way as above. The recycling results are collated in Table 3 below. The initial activity of the system is maintained at 2100 h$^{-1}$.

TABLE 3

| TIME (h) | CONVERSION (%) | n/i | S ald (%) | Isom (%) |
|---|---|---|---|---|
| 0.5 | 56 | 3.8 | 95 | 5 |
| 1 | 90 | 3.8 | 95 | 5 |
| 2 | 100 | 3.6 | 96 | 4 |

Two additional recycling operations were carried out under the conditions defined above, and the results are collated in Tables 4 and 5 below.

TABLE 4

| TIME (h) | CONVERSION (%) | n/i | S ald (%) | Isom (%) |
|---|---|---|---|---|
| 1 | 93 | 3.4 | 95 | 5 |
| 2 | 100 | 3.2 | 96 | 4 |

TABLE 5

| TIME (h) | CONVERSION (%) | n/i | S ald (%) | Isom (%) |
|---|---|---|---|---|
| 1 | 95 | 3.2 | 95 | 5 |

Examples 10–11

Recycling in the Presence of tris[2-(1H,1H,2H,2H-Perfluorodecyl)phenyl] Phosphite and tris[2,4-bis-(1H,1H2H,2H-Perfluorodecyl)phenyl] Phosphite At the end of the catalytic tests in Examples 6 and 8, three recycling tests were carried out under the same conditions as in Example 9. The results obtained in the third recycling are presented in Table 6 below.

TABLE 6

| Example No. | Fluorine-containing phosphite | Time (h) | Conversion | n/i | S ald[e] (%) | Isom[f] (%) |
|---|---|---|---|---|---|---|
| 10 | 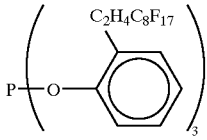 | 0.1 | 60 | 1.9 | 70 | 30 |
| 11 | 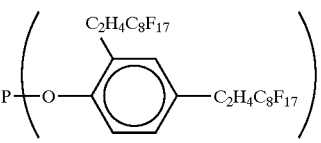 | 0.1 | 90 | 1.9 | 75 | 25 |

Examples 12 to 14
Hydroformylation of Internal Fatty Olefins in a Florinated Two-chase Medium in the Presence of tris[4-(1H,1H,2H,2H-Perfluorodecyl)phenyl] Phosphite The hydroformylation of olefins with an internal double bond was carried out under the same conditions as in Examples 6–8, in the presence of tris[4-(1H,1H,2H,2H-perfluorodecyl)phenyl] phosphite, and the results are in Table 7.

TABLE 7

| Example No. | Olefin | Time (h) | Conversion (%) | Distribution of the aldehydes as a % of position | | | | S ald[e] (%) | Isom[f] (%) |
| | | | | 1 | 2 | 3 | 4 | | |
|---|---|---|---|---|---|---|---|---|---|
| 12 | Cyclohexene | 6 | 25 | — | | | — | 100 | — |
| 13 | 2-Octene | 0.5 | 70 | — | — | — | — | 82 | 18 |
| | | 1.5 | 95 | 5 | 60 | 30 | 5 | | |
| 14 | 4-Octene | 2.5 | 95 | 8 | 28 | 26 | 38 | 85 | 15 |

What is claimed:
1. Tris[2-(1H,1H,2H,2H-perfluorodecyl) phenyl] phosphite.
2. Tris[2,4-bis(1H,1H,2H,2H-perfluorodecyl) phenyl] phosphite.

* * * * *